United States Patent [19]
Stinn et al.

[11] Patent Number: 5,898,012
[45] Date of Patent: Apr. 27, 1999

[54] COMPOSITIONS COMPRISING INORGANIC OXIDE AND PROCESS FOR PRODUCING MERCAPTANS

[75] Inventors: Dean E. Stinn; Harold J. Swindell; Donald H. Kubicek; Marvin M. Johnson, all of Bartlesville, Okla.

[73] Assignee: Phillips Petroleum Company, Bartlesville, Okla.

[21] Appl. No.: 08/956,550

[22] Filed: Oct. 23, 1997

Related U.S. Application Data

[62] Division of application No. 08/620,147, Mar. 22, 1996, Pat. No. 5,733,836.

[51] Int. Cl.⁶ .................................................. C07C 319/04
[52] U.S. Cl. .................................................. 568/71
[58] Field of Search .................................... 568/71

[56] References Cited

U.S. PATENT DOCUMENTS

| | | |
|---|---|---|
| 3,053,902 | 9/1962 | Doumani . |
| 3,697,602 | 10/1972 | Schreyer . |
| 3,994,980 | 11/1976 | Kubicek . |
| 5,405,820 | 4/1995 | Clark . |

OTHER PUBLICATIONS

CA:113:211327 abs of "Catalyst screening for methyl mercaptan synthesis", by Andrislki, Organika, vol. date 1987–1988 pp. 21–29, 1989.

CA:110: 7614 abs of "Synthesis of methyl mercaptan from methanol and hydrogen sulfide in the presence of acid catalysts" by Mashkina, Kinet Katal 29(3), pp. 596–602, 1988.

CA:68:77739 abs of "Catalytic process for preparing mercaptans", RO 44346, Dec. 1966.

*Primary Examiner*—Gary Geist
*Assistant Examiner*—Jean F. Vollano
*Attorney, Agent, or Firm*—Lucas K. Shay

[57] ABSTRACT

A composition comprises at least one inorganic oxide and an oxygen-containing metal compound selected from the group consisting of a metal hydroxide, a metal oxide, and combinations of any two or more thereof. The composition can be optionally supported on a support such as an alumina. A process for producing mercaptans comprises contacting an alcohol with hydrogen sulfide in the presence of the composition under a condition sufficient to produce a mercaptan.

19 Claims, No Drawings

COMPOSITIONS COMPRISING INORGANIC OXIDE AND PROCESS FOR PRODUCING MERCAPTANS

This application is a Division of application Ser. No. 08/620,147, filed Mar. 22, 1996 now U.S. Pat. No. 5,733,836.

FIELD OF THE INVENTION

The present invention relates to a composition which comprises an inorganic oxide and to a process for using the composition for producing a mercaptan.

BACKGROUND OF THE INVENTION

An inorganic oxide or a mixture of inorganic oxides is known to catalyze chemical reactions. For example, thorium oxide can be used to catalyze the reaction of an alcohol and hydrogen sulfide for the production of a mercaptan.

Mercaptans are a class of important industrial chemicals. One of the main uses of a mercaptan is a polymerization modifier or chain terminator to control the molecular weight of a polymer. Mercaptans, especially lower molecular weight mercaptans, can also be used as intermediates in the production of agricultural chemicals such as, for example, insecticides, acaricides, herbicides, and defoliants. Methyl mercaptan can further be combined with acrolein for the commercial production of methionine, an essential amino acid. Other uses of mercaptans include odorants in natural gas, liquefied petroleum gas, rubber vulcanization accelerators, epoxy-curing agents, froth collectors, and medicinal uses.

Because of the wide use of mercaptans, there is an ever-increasing need for improving the production of mercaptan. Often seemingly small improvements translate into large reduction in manufacturing costs of mercaptans thereby saving consumers.

SUMMARY OF THE INVENTION

An object of the present invention is to provide a composition which can be used for producing mercaptans. Another object of the invention is to provide a process for producing mercaptans. A further object of the invention is to provide a process for producing mercaptans having improved selectivity. Other objects and features will become more apparent as the invention is more fully disclosed hereinbelow.

According to a first embodiment of the present invention, a composition which can be used for producing a mercaptan is provided. The composition comprises, consists essentially of, or consists of at least one inorganic oxide and an oxygen-containing metal compound, optionally supported on a support such as an alumina and a silica wherein the oxygen-containing metal compound is selected from metal hydroxides, metal oxides, and combinations of any two or more thereof.

According to a second embodiment of the present invention, a process which can be used for producing a mercaptan is provided. The process comprises, consists essentially of, or consists of contacting an alcohol, in the presence of a composition, with hydrogen sulfide under a condition effective to produce a mercaptan wherein the composition comprises, consists essentially of, or consists of at least one inorganic oxides and an oxygen-containing metal compound, optionally supported on a support such as an alumina and a silica wherein the oxygen-containing metal compound is selected from metal hydroxides, metal oxides, and combinations of any two or more thereof; and the composition is present in a sufficient amount to effect the production of a mercaptan.

DETAILED DESCRIPTION OF THE INVENTION

According to the first embodiment of the invention, one of the components of the invention composition is an inorganic oxide. Any inorganic oxide can be used in the present invention as long as the inorganic oxide can effect the catalysis of the reaction of hydrogen sulfide and an alcohol for the production of a mercaptan. Generally, the inorganic oxides can be the oxides of transition metals such as titanium, zirconium, hafnium, vanadium, chromium, molybdenum, tungsten, manganese, technetium, iron, ruthenium, cobalt, rhodium, iridium, nickel, palladium, platinum, copper, zinc, and cadium, and other oxides such as alumina, and combinations of any two or more thereof. Generally, any oxidation states of these metals can be used. The presently preferred inorganic oxide is molybdenum oxide or a combination of a cobalt oxide and molybdenum oxide wherein the oxidation state of cobalt and molybdenum can be any available oxidation states. The presently most preferred combination of inorganic oxides is cobalt oxide and molybdenum oxide, an example of which is cobalt molybdate or HDS-22 which is commercially available from Criterion Catalyst Company, Michigan City, Ind. wherein the oxidation state of cobalt and molybdenum is 2 and 6, respectively.

An inorganic oxide or combination of inorganic oxides can be supported on an inorganic support such as an alumina or silica. Any form of support can be used. For example, alumina can be an $\alpha$-alumina, $\beta$-alumina, $\gamma$-alumina, or combinations of any two or more thereof. Generally, a supported combination of organic oxides is commercially available. The HDS-22 disclosed above is a combination of inorganic oxides supported on alumina.

Any metal hydroxide or metal oxide can be used in the present invention. The presently preferred metal hydroxide or metal oxide is an alkali metal hydroxide, an alkaline earth metal hydroxide, an alkali metal oxide, an alkaline earth metal oxide, or combinations of any two or more thereof. Examples of metal hydroxides include, but are not limited to sodium hydroxide, lithium hydroxide, potassium hydroxide, magnesium hydroxide, calcium hydroxide, and combinations of any two or more thereof. Examples of metal oxides include, but are not limited to sodium oxide, lithium oxides, potassium oxide, magnesium oxide, calcium oxide, and combinations of any two or more thereof. The presently most preferred metal hydroxide is potassium hydroxide for it is inexpensive and readily available. The metal hydroxide or metal oxide can be physically attached such as, for example, impregnated to the inorganic oxide or the combination of inorganic oxides, or the support, or combinations thereof.

Each inorganic oxide can be present in the invention composition in any weight percent (%) of the composition so long as the weight percent can effect the catalysis of the reaction of hydrogen sulfide and an alcohol. Generally, the weight percent can be in the range of from about 1 to about 99, preferably about 1 to about 90, more preferably about 2 to about 80, and most preferably 2 to 70%. Similarly, the amount of the oxygen-containing metal compound can be any sufficient amount that can effect the catalysis of the reaction of hydrogen sulfide and an alcohol. Generally, the amount of the oxygen-containing metal compound can be in the range of from about 0.01 to about 20%, preferably about 0.1 to about 15%, and most preferably 0.5 to 10% based on the total weight % the composition being 100%. The amount of support, if employed, can be any amount so long as the composition can be supported. Generally such amount can be in the range of from about 50 to about 99, preferably 50 to about 90, and most preferably 50 to 85% based on the total weight % the composition being 100%.

According to the present invention, the composition can be produced by any methods known to one skilled in the art. For example, an oxygen-containing metal compound such as a metal hydroxide can be first dissolved or substantially dissolved in a proper solvent such as, for example, water to form a solution or a suspension. The solution or suspension can then be combined with an inorganic oxide or a combination of inorganic oxides for about 1 minute to about 10 hours, preferably about 1 minute to about 5 hours, and most preferably 5 minutes to one hour to form a solid or slurry mixture in an aqueous solution. The mixture can then be separated from the aqueous solution. The separation of the solid or slurry mixture from the aqueous solution can be carried out by any methods known to one skilled in the art such as, for example, filtration, decantation, centrifugation, evaporation, and combinations of any two or more thereof. The temperature required for forming the mixture can be any temperature so long as the temperature can effect the formation of a composition which can catalyze the reaction of hydrogen sulfide and an alcohol.

After the mixture is separated, the mixture can be washed, if desired, with the same solvent followed by removing the solvent. Any excess solvent associated with the composition can be further removed by, for example, drying in a drying means such as, for example, a drying oven at a temperature, dependent on the type of solvent, generally in the range of from about 50 to about 300° C., preferably about 75 to about 250° C., and most preferably 100 to 200° C. for about 1 to about 30 hours depending on the quantity of solvent and dryness desired. Thereafter, the composition can be calcined for about 5 minutes to about 10 hours, preferably about 10 minutes to about 5 hours, and most preferably 10 minutes to 3 hours at a temperature in the range of from about 200 to about 1,500° C., preferably about 300 to about 1,000° C., and most preferably 400 to 700° C. It should be noted that, the composition of the present invention can be produced by a process under any pressure. Generally, it is preferred that the process be carried out under atmospheric pressure.

An inorganic oxide can be first supported on a support followed by combining an oxygen-containing metal compound with the supported inorganic oxide using the process disclosed hereinabove. Alternatively, an inorganic oxide can be first combined with an oxygen-containing metal compound as disclosed hereinabove and the resulting composition is then supported on a support. The calcination process disclosed above can also be used to prepare a supported composition. Because the preparation of a supported composition is well known to one skilled in the art, the description of which is omitted herein. For example U.S. Pat. No. 4,493,715 discloses a procedure for supporting alkali metal compound on alumina, description of which is incorporated herein by reference.

According to the second embodiment of the present invention, a process which can be used for producing a mercaptan is provided. The process comprises contacting hydrogen sulfide, in the presence of a catalyst composition, with an alcohol. The catalyst composition useful for the process is the same composition as disclosed in the first embodiment of the invention.

Mercaptans that can be produced by the process of the invention have the formula of $R(SH)_n$ in which n is 1 or greater and R is a hydrocarbyl radical which can be selected from the group consisting of alkyl radicals, alkenyl radicals, aryl radicals, alkaryl radicals, aralkyl radicals, and combinations of any two or more thereof. Each radical can have 1 to about 30, preferably to about 25, and most preferably to 20 carbon atoms. The radicals can be linear, branched, cyclic, substituted, or combinations of any two or more thereof.

Examples of suitable mercaptans include, but are not limited to, methyl mercaptan, ethyl mercaptan, propyl mercaptan, isopropyl mercaptan, butyl mercaptan, isobutyl mercaptan, t-butyl mercaptan, amyl mercaptan, hexyl mercaptan, cyclohexyl mercaptan, octyl mercaptan, nonyl mercaptan, decyl mercaptan, dodecyl mercaptan, t-dodecyl mercaptan, benzyl mercaptan, thiophenol, tolyl mercaptan, methanedithiol, 1,2-ethanedithiol, 1,2,3-propanetrithiol, 1,5-pentanedithiol, and combinations of any two or more thereof. The presently preferred is methyl mercaptan for it is widely used commercially.

Any alcohols that can react with hydrogen sulfide to produce a mercaptan can be employed in the present invention. Generally a suitable alcohol has the formula of $R(OH)_n$ in which R and n are the same as those disclosed above. Examples of suitable alcohols include, but are not limited to, methyl alcohol, ethyl alcohol, propyl alcohol, isopropyl alcohol, butyl alcohol, isobutyl alcohol, t-butyl alcohol, amyl alcohol, hexyl alcohol, cyclohexyl alcohol, octyl alcohol, nonyl alcohol, decyl alcohol, dodecyl alcohol, t-dodecyl alcohol, benzyl alcohol, phenol, tolyl alcohol, heptanetriol, ethylene glycol, propanetriol, glycerol, and combinations of any two or more thereof. The presently preferred is methyl alcohol or methanol, for it is widely used commercially.

According to the present invention, the molar ratio of hydrogen sulfide to an alcohol can be any ratio so long as the ratio can effect the production of a mercaptan. The ratio can be in the range of from about 0.01:1 to about 50:1, preferably about 1:1 to about 20:2, and most preferably 1:1 to 10:1. The feed rate, if the process is carried out continuously, can be any rate that is sufficient to effect the production of a mercaptan. Generally, the feed rate can be in the range of from about 0.1 to about 20, preferably about 0.1 to about 15, and most preferably 0.5 to 10 weight hourly space velocity of alcohol feed based on catalyst composition weight (g feed per hour per g catalyst). Hydrogen sulfide and alcohol can be precombined and then fed to a reactor, or individually fed to the reactor. If the process is carried out in a batch mode, the amount of the catalyst composition required is any amount that can catalyze the reaction of hydrogen sulfide and an alcohol. The amount can generally be in the range of from about 0.001 to about 5 g of the catalyst composition per g of feed based on alcohol.

According to the present invention, the contacting of hydrogen sulfide and an alcohol can be carried out under any condition so long as the condition is sufficient to effect the production of a mercaptan compound. Generally, such a condition can include a temperature in the range of from about 100° C. to about 500° C., preferably about 150° C. to about 350° C., and most preferably 200° C. to 300° C.; a pressure in the range of from about 0.5 atmosphere (atm) to about 60 atm, preferably about 1 atm to about 50 atm, and most preferably 5 atm to 40 atm; and a contacting time of from about 1 to about 25 hours, preferably about 1 to about 20 hours, and most preferably 1 to 15 hours.

The process of the invention can also be carried out in the presence of a solvent if such a solvent can facilitate the contacting of hydrogen sulfide with an alcohol. Such a solvent can be, for example, a hydrocarbon, an ether, or combinations of any two or more thereof. If a solvent is employed, the quantity of the solvent can be any quantity that can facilitate the contacting of hydrogen sulfide with an alcohol. The molar ratio of a solvent to hydrogen sulfide can be in the range of from about 0.01:1 to about 100:1.

The process of the invention can be carried out batchwise, continuously, semicontinuously, or combinations of any two or more thereof. Any reactor that can be used for chemical reactions under elevated pressure and temperature can also be used in the process of the present invention. Because a process mode and reactor depend on the preference of one skilled in the art, the description of which is omitted herein.

Upon completion of the contacting of hydrogen sulfide and an alcohol, the mercaptans produced can be used as is, or further processed such as, for example, separated and recovered from the contacting medium. Any means known to one skilled in the art such as, for example distillation, fractionation, membrane filtration, extraction, extractive distillation, and combinations of any two or more thereof can be used for further process, separation, or recovery of the mercaptans. Because it is not in the scope of the present invention, description of which is omitted herein for the interest of brevity.

The following non-limiting examples are provided to illustrate the process of the invention.

EXAMPLE I

This example illustrates the process for the production of the composition of the present invention.

Eight hundred grams of cobalt molybdate on alumina (hereinafter cobalt moly), purchased from Criterion Catalyst Company, L. P., Michigan City, Ind. under a trade name of "HDS-22" (4.5 weight percent (%) of cobalt oxide (CoO) and 15.5% of molybdenum oxide ($MoO_3$) on alumina), was added to a 4-liter beaker. A potassium hydroxide solution made by dissolving 12 g KOH in 1 liter of distilled water was then added to the beaker to form a mixture. The mixture was stirred for 30 minutes at 25° C. Thereafter, the aqueous portion was poured off from the beaker. A wet was obtained and was washed with 1 liter of distilled water. Upon pouring off the water, the resultant solid was dried in an oven at 150° C. for 15 hours. The dried solid was then calcined at 500° C. for 1 hour in a programmed oven, ramping from ambient temperature (about 25° C.) at 3° C. per minute to 150° C., then 5° C. per minute to 500° C. (the solid was calcined for 1 hour at 500° C.). The calcined composition was used in Example II.

EXAMPLE II

This example illustrates a process for preparing methyl mercaptan using the composition prepared in Example I.

The reactor used in this study consisted of a jacked, 316 stainless steel pipe (¾" I.D.×29" long). The jacket of the reactor was connected to a hot oil circulation unit for control of the reactor temperature. A feed tank was charged prior to each run with desired reactants. The reactants were fed from the feed tank to the reactor by the use of a Lapp metering pump. A preheater was used to heat the reactant being charged to the reactor and was operated in such a fashion so as to introduce the feed to the reactor at a temperature below that of the circulating hot oil. The hot oil unit was operated at a temperature sufficient to initiate and sustain the reaction. The pressure on the reactor was maintained by the use of a back pressure regulator. The reactor effluent was sent to the flare system with portions being periodically sent to a gas chromatograph for analysis.

The catalyst used was the invention composition described in Example I which has been extruded to a 1.3 millimeter tri-lobed extrudate. The catalyst was loaded into about the center half of the reactor. Both ends of the reactor were packed with glass beads (inert packing).

A typical run was conducted as follows. To the feed tank was charged 1140 grams of hydrogen sulfide and 179 grams of methanol. The above mixture was pumped through the reactor at such a rate to give a weight hourly space velocity of methanol equal to 1.0 based upon the catalyst loading. The temperature of the hot oil system was operated at the desired temperature. The results are shown in the following Table.

| Run[a] | Hot Oil Temp (° C.) | MeSH Selectivity | MeOH Conversion | Ratio of MeSH:DMS |
|---|---|---|---|---|
| 1 | 235 | 88.5% | 99+% | 8.4 |
| 2 | 245 | 83.9% | 99+% | 5.3 |
| 3 | 235 | 89.1% | 99+% | 10.6 |
| 4 | 245 | 85.9% | 99+% | 7.1 |

[a]Runs 1 and 2 were control runs in which commercial HDS-22 catalyst was used. Runs 3 and 4 were invention runs using the invention composition described in Example I. The molar ratio of hydrogen sulfide to methanol was 6:1.

Comparing the results of runs 1 and 3 shown above, it is clear that the selectivity to methyl mercaptan improved to 89.1% using the invention composition as compared to 88.5% in control run. More importantly, the ratio of methyl mercaptan to dimethyl sulfide significantly increased. Increasing the molar ratio of methyl mercaptan to dimethyl sulfide, in this example, by more than 25% is an indication that methanol was more efficiently converted to methyl mercaptan using the invention process as compared to the control run. Increase in the molar ratio of methyl mercaptan to dimethyl sulfide would also greatly facilitate the separation of methyl mercaptan from the reaction mixture thereby lowering the manufacturing costs of methyl mercaptan. Similar results were obtained with higher reaction temperature of 245° C. (runs 2 and 4).

The results shown in the above example clearly demonstrate that the present invention is well adapted to carry out the objects and attain the end and advantages mentioned as well as those inherent therein. While modifications may be made by those skilled in the art, such modifications are encompassed within the spirit of the present invention as defined by the disclosure and the claims.

That which is claimed:

1. A process comprising contacting hydrogen sulfide, in the presence of a composition, with an alcohol under a condition effective to produce a mercaptan wherein said composition comprises at least one inorganic oxide, selected from the group consisting of zirconium oxide, hafnium oxide, vanadium oxide, chromium oxide, molbdenum oxide, tungsten oxide, manganese oxide, technetium oxide, iron oxide, ruthenium oxide, cobalt oxide, rhodium oxide, iridium oxide, nickel oxide, palladium oxide, platinum oxide, copper oxide, zinc oxide, cadium oxide and combinations of any two or more thereof. and an oxygen-containing metal compound selected from the group consisting of metal hydroxides, alkali metal oxides, alkaline earth metal oxides, and combinations of any two or more thereof; said process is carried out at a temperature in the range of from 200° C. to 300° C.; said composition is supported on a support; and said composition is present in a sufficient amount to effect the production of a mercaptan.

2. A process according to claim 1 wherein said inorganic oxide is a combination of cobalt oxide and molybdenum oxide.

3. A process according to claim 1 wherein said metal hydroxide is selected from the group consisting of alkali oxygen-containing metal hydroxides, alkaline earth metal compound, and combinations of any two or more thereof.

4. A process according to claim 1 wherein said oxygen-containing metal compound is potassium hydroxide.

5. A process according to claim 1 wherein said support is selected from the group consisting of aluminas, silica, and combinations of any two or more thereof.

6. A process according to claim 5 wherein said support is an alumina.

7. A process according to claim 2 wherein said support is an alumina.

8. A process according to claim 4 wherein said support is an alumina.

9. A process according to claim 1 wherein said inorganic oxide is present in said composition in the range of from about 16 to about 90 weight %.

10. A process according to claim 1 wherein said oxygen-containing metal compound is present in said composition in the range of from about 0.1 to about 15 weight %.

11. A process comprising contacting hydrogen sulfide, in the presence of a composition, with an alcohol under a condition effective to produce a mercaptan wherein said composition comprises at least one inorganic oxide and an oxygen-containing metal compound wherein:

said composition is supported on a support selected from the group consisting of aluminas, silica, and combinations of any two or more thereof;

said inorganic oxide is selected from the group consisting of titanium oxide, zirconium oxide, hafnium oxide, vanadium oxide, chromium oxide, molybdenum oxide, tungsten oxide, manganese oxide, technetium oxide, iron oxide, ruthenium oxide, cobalt oxide, rhodium oxide, iridium oxide, nickel oxide, palladium oxide, platinum oxide, copper oxide, zinc oxide, cadmium oxide, alumina, and combinations of any two or more thereof;

said oxygen-containing metal compound is selected from the group consisting of alkali metal hydroxides, alkaline earth metal hydroxides, alkali metal oxides, alkaline earth metal oxides, and combinations of any two or more thereof;

said inorganic oxide is present in said composition in the range of from about 1 to about 99 weight %; and said oxygen-containing metal compound is present in said composition in the range of from about 0.01 to about 20 weight %.

12. A process according to claim 11 wherein said inorganic oxide is a combination of cobalt oxide and molybdenum oxide and each inorganic oxide is present in said composition in the range of from 2 to 80 weight %; said support is an alumina; and said oxygen-containing metal compound is potassium hydroxide and is present in said composition in the range of from 0.5 to 10 weight %.

13. A process according to claim 11 wherein said alcohol is selected from the group consisting of methyl alcohol, ethyl alcohol, propyl alcohol, isopropyl alcohol, butyl alcohol, isobutyl alcohol, t-butyl alcohol, amyl alcohol, hexyl alcohol, cyclohexyl alcohol, octyl alcohol, nonyl alcohol, decyl alcohol, dodecyl alcohol, t-dodecyl alcohol, benzyl alcohol, phenol, tolyl alcohol, heptanetriol, ethylene glycol, propanetriol, glycerol, and combinations of any two or more thereof.

14. A process according to claim 13 wherein said alcohol is methyl alcohol.

15. A process for producing a mercaptan comprising contacting hydrogen sulfide, in the presence of a catalyst comprising alumina-supported cobalt oxide and molybdenum oxide having impregnated thereon potassium, with an alcohol under a condition sufficient to effect the production of a mercaptan wherein said cobalt oxide and molybdenum oxide are each present in said catalyst in the range of from 2 to 80 weight %; and said potassium is present in said composition in the range of from 0.5 to 10 weight %.

16. A process according to claim 15 wherein said mercaptan is methyl mercaptan and said alcohol is methyl alcohol.

17. A process according to claim 12 wherein said process is carried out at a temperature in the range of from 200° C. to 300° C.

18. A process according to claim 14 wherein said process is carried out at a temperature in the range of from 200° C. to 300° C.

19. A process according to claim 16 wherein said process is carried out at a temperature in the range of from 200° C. to 300° C.

* * * * *